(12) United States Patent
Rasche et al.

(10) Patent No.: US 10,234,529 B2
(45) Date of Patent: Mar. 19, 2019

(54) METHOD FOR PRODUCING MAGNET RESONANCE TOMOGRAPHY RECORDINGS OF CYCLIC MOVEMENT

(71) Applicant: SIRONA DENTAL SYSTEMS GMBH, Bensheim (DE)

(72) Inventors: Volker Rasche, Erbach (DE); Stefan Wundrak, Gronau (DE)

(73) Assignee: DENTSPLY SIRONA INC., York, PA (US)

( * ) Notice: Subject to any disclaimer, the term of this patent is extended or adjusted under 35 U.S.C. 154(b) by 170 days.

(21) Appl. No.: 15/355,104

(22) PCT Filed: May 19, 2015

(86) PCT No.: PCT/EP2015/060956
§ 371 (c)(1),
(2) Date: Nov. 18, 2016

(87) PCT Pub. No.: WO2015/177117
PCT Pub. Date: Nov. 26, 2015

(65) Prior Publication Data
US 2017/0123033 A1  May 4, 2017

(30) Foreign Application Priority Data
May 19, 2014 (DE) .................. 10 2014 209 437

(51) Int. Cl.
*G01R 33/56* (2006.01)
*G01R 33/563* (2006.01)
(Continued)

(52) U.S. Cl.
CPC ...... *G01R 33/56391* (2013.01); *A61B 5/1128* (2013.01); *A61B 5/4542* (2013.01);
(Continued)

(58) Field of Classification Search
CPC .............. G01R 33/563; G01R 33/5635; G01R 33/56375; G01R 33/56391; G01R 33/56509; G01R 33/5608
(Continued)

(56) References Cited

U.S. PATENT DOCUMENTS 6,937,696 B1 * 8/2005 Mostafavi .............. A61B 5/113
378/65
2004/0082846 A1 * 4/2004 Johnson ............. A61B 5/02014
600/410
(Continued)

*Primary Examiner* — Patrick Assouad
*Assistant Examiner* — Demetrius R Pretlow
(74) *Attorney, Agent, or Firm* — Dentsply Sirona Inc.

(57) ABSTRACT

Disclosed is a method for producing magnetic resonance tomography images (B) of at least one phase of a cyclic movement, comprising the method steps: production of raw data sets (r1, . . . , rx) of the cyclic movement during a recording period (T) having radial or almost radial k-space part trajectories (k1, . . . , kx); reconstruction of a series of intermediate images (z1, . . . , zy), each from at least one raw data set (r1, . . . , rx) with high time resolution at least for each region (region of interest, ROI) of the raw data sets (r1, . . . , rx); calculation of a distance matrix (D) from the series of intermediate images (z1, . . . , zy), wherein each matrix element (D) corresponds to the distance of a first intermediate image (z1, . . . , zy) of the series to the first or a further intermediate image (z1, . . . , zy) of the series; fitting of functions (vi, . . . , vz) to structures forming in the distance matrix (D) by means of an active contour method and reconstruction of at least one image (B) from the raw data sets (r1, . . . , rx), said raw data sets corresponding to intersection (S) of the fitted curves (v1, . . . , vz) with a line of the distance matrix (D).

7 Claims, 1 Drawing Sheet

(51) Int. Cl.
*G01R 33/48* (2006.01)
*G01R 33/565* (2006.01)
*A61B 5/11* (2006.01)
*A61B 5/00* (2006.01)
*A61B 5/055* (2006.01)

(52) U.S. Cl.
CPC ..... *G01R 33/4824* (2013.01); *G01R 33/5608* (2013.01); *G01R 33/56509* (2013.01); *A61B 5/055* (2013.01)

(58) Field of Classification Search
USPC ........................................................ 324/309
See application file for complete search history.

(56) References Cited

U.S. PATENT DOCUMENTS

| | | | | |
|---|---|---|---|---|
| 2005/0207538 A1* | 9/2005 | Mollus | ................... | A61B 6/541 378/132 |
| 2006/0224062 A1* | 10/2006 | Aggarwal | .......... | G01R 33/5673 600/413 |
| 2008/0219527 A1* | 9/2008 | Lavi | .......... | G06T 7/12 382/128 |
| 2012/0063671 A1* | 3/2012 | Yamada | ............. | G06K 9/00248 382/154 |
| 2012/0078083 A1* | 3/2012 | McConnell | ............ | A61B 5/055 600/413 |
| 2013/0113482 A1* | 5/2013 | Speier | ................ | G01R 33/4818 324/309 |
| 2016/0307331 A1* | 10/2016 | Mollus | .................... | G06T 7/344 |

* cited by examiner

METHOD FOR PRODUCING MAGNET RESONANCE TOMOGRAPHY RECORDINGS OF CYCLIC MOVEMENT

TECHNICAL FIELD

The present disclosure relates to a method for producing magnetic resonance tomography recordings of at least one phase of a cyclic movement.

BACKGROUND

In order to produce magnetic resonance tomography images of different phases of a movement of an object, such as of the masticatory movement of a jaw, images are frequently taken of individual positions of the movement. For this purpose, a device for fixing the object, such as the jaw, in the various positions is required. As a result of the fixing, sufficient magnetic resonance tomography data for an image can be produced for each individual position. However, this manner of taking images is very complex and possible dynamic effects, which only occur during a real motion sequence, cannot be represented.

If the movement is sufficiently slow, for example, if the masticatory movement is performed slowly enough, it is also possible to produce sufficient magnetic resonance tomography data for each movement phase during a single movement cycle. This is described for example in "Real-Time Magnetic Resonance Imaging of Temporomandibular Joint Dynamics," S. Zhang et al., published in The Open Medical Imaging Journal, 5, 1-7, 2011.

However, the slow performance of a masticatory movement, for example, is very challenging for a patient and must be practiced or assisted. In addition, dynamic effects that only occur at the normal speed of movement cannot be represented with this method.

In a cyclic movement, it is furthermore possible to generate data sets over several cycles of the movement and subsequently to assign a phase of the movement in each case to the data sets. In this way, all data sets corresponding to the phase can be taken as the basis for an image of the corresponding movement phase.

To make assignment possible, the positions of the movement can, for example, be recorded using a device. However, the costs resulting from the additional device are disadvantageous.

From "Adaptive Averaging Applied to Dynamic Imaging of the Soft Palate" by A. D. Scott et al., published in Magnetic Resonance in Medicine, volume 70, pages 865-874, September 2013, a method for producing recordings of movements is known, which determines correlation coefficients between individual real-time images.

Based on the correlation coefficients, real-time images of the same movement phase are identified and taken as the basis for an overall image of this movement phase.

The method described thus correlates images with a low signal-to-noise ratio (SNR), without a cyclic movement having to be present for this purpose. The images with a high correlation coefficient are averaged in order to increase the SNR. The method does however have the disadvantage that the temporal and spatial resolution is limited due to the dense scanning of a k-space required to obtain artifact-free images. The spatial resolution is, for example, between 1.6×1.6 and 2.0×2.0 mm^2. The temporal resolution can be 50-111 ms, for example, due to parallel imaging with several coils. For measurements with one coil, the temporal resolution would only be 150-300 ms. The required spatial and temporal resolutions for TMJ (temporomandibular joint dysfunction) recordings are at most 0.75×0.75 m^2 and 100 ms respectively.

Another disadvantage is that incorrect or ambiguous maxima of the pairwise correlation can lead to distorted results and this reduces the robustness of the method.

SUMMARY

The task of the present disclosure is to provide a particularly simple and reliable method for producing recordings of individual movement phases of a cyclic movement with a high temporal and spatial resolution.

This task is solved by a method for producing magnetic resonance tomography images of at least one phase of a cyclic movement, comprising the following method steps: Production of raw data sets of a cyclic movement during a recording period (T) having k-space sub-trajectories; reconstruction of a series of at least two intermediate images, each from at least one raw data set, at least for each region (region of interest, ROI) of the raw data sets; calculation of a distance matrix from the series of intermediate images, wherein each matrix element D corresponds to the distance of an intermediate image of the series to itself or to a further intermediate image of the series; adaption or fitting or approximation of curves or functions to structures forming in the distance matrix; and reconstruction of at least one image from the raw data sets, said raw data sets corresponding to an intersection of the fitted curves or functions with the entries, relating to an intermediate image, of the distance matrix.

DETAILED DESCRIPTION

The k-space sub-trajectories can be radial or almost radial. The reconstruction of the intermediate images can be carried out with a high temporal resolution.

The distance matrix can be a two-dimensional, a three-dimensional, or a multi-dimensional distance matrix.

In a two-dimensional distance matrix, the structures can be lines.

The intersection can have several intersection points.

The adaption of the curves or functions to lines forming in the distance matrix D can for example be carried out via maximization of the line integrals. For example, an active contour method or another curve-fitting method can be used for maximization of the line integrals.

Alternatively thereto, the so-called brute force method or the exhaustion method can also be used. In this method for an algorithmic solution of a problem, all potential solutions are tried out until the right one is found.

The method according to the present disclosure allows for the production of magnetic resonance tomography images of an object in individual phases of a repeating movement, without increased requirements having to be imposed on the performance of the movement or the speed of the data acquisition. For example, a mandibular joint can be imaged in the different phases of a masticatory movement performed continuously at normal speed or of a repeating speech movement by measuring the movement over several cycles.

For the magnetic resonance tomography measurement, a chronological sequence, called a measuring sequence, of combinations of magnetic gradient fields, high-frequency pulses, and signal-receiving times that are run through once or several times during the recording period is used. The measuring sequence for example specifies the chronological sequences of the frequencies and field strengths of the gradient fields and frequency pulses.

From the selected measuring sequence, the k-space trajectory results, i.e. the sequence of measuring points in the k-space, where a linear vector space Fourier-transformed relative to the position space, of a two- or three-dimensional complex wave vector k is called a k-space. Accordingly, the designation "wave vector space" is in common use for the k-space.

According to the disclosure, a k-space trajectory composed of radial or almost radial k-space sub-trajectories is used to scan the k-space. "Radial k-space sub-trajectory" refers to individual lines running through the center of the k-space, with measuring points. These lines can run virtually as circle diameters from the outside through the center to the outside again and are also called "spokes" or "center-out lines." A special case is constituted by "radial center-out" k-space sub-trajectories, which run only from the center to the outside.

An example of almost radial k-space trajectories is PROPELLER EPI (Magn. Reson. Med. 2005 November; 54(5): 1232-40. "PROPELLER EPI: an MRI technique suitable for diffusion tensor imaging at high field strength with reduced geometric distortions," Wang et al.) The raw data sets measured during the recording period during the scanning of the k-space are stored for example one after the other in a storage unit.

A raw data set can be the signal recorded during the measurement of a single point in the k-space. A raw data set can also contain the signals recorded during the measurement of a k-space sub-trajectory or the signals of any other grouping of measuring points in the k-space. A k-space sub-trajectory consisting of several measuring points or the measurement data recorded at the corresponding measuring points are frequently stored as a raw data set.

Intermediate images with high temporal resolution are reconstructed from the raw data sets. A high temporal resolution can be achieved by a low spatial resolution or by a high spatial resolution with scan artifacts. The temporal resolution is for example increased by reducing the number of k-space sub-trajectories or raw data sets per image.

By a combination with parallel imaging, the number of k-space sub-trajectories can be reduced further.

The reconstruction can be carried out for the entire local recording window. By limiting the reconstruction to a region of interest (ROI), computational effort can be reduced.

Furthermore, influences for example from the regions surrounding a moving joint or object can thereby be reduced and/or prevented and the quality of the recording to be produced improved. The totality of these reconstructed intermediate images is termed a series of intermediate images.

From the series of intermediate images, a distance matrix is calculated, wherein for each intermediate image of the series, the distance to each of the other intermediate images of the series and to itself is calculated using a certain distance metric or norm and stored as matrix element of the distance matrix. For example, a Euclidean distance matrix with the Euclidean distances of the intermediate images to each other as matrix elements can be used:

$$D=(d_{1j}); d_{1j}=-\|z_1-z_j\|_2$$

However, any other norm which describes the similarity between two images and thus can serve as a measure of similarity can also be used.

The matrix elements corresponding to a comparison of each intermediate image with itself and located on the main diagonal contain minimum or maximum values depending on the definition of the matrix elements due to the perfect equality. In an illustration of the distance matrix, a straight line along the main diagonal can therefore be clearly seen. Parallel as well as orthogonal to this main diagonal, additional similar structures or lines form due to the repetition of the movement. The more consistently the movement repeats, the more similar the forming lines of the main diagonals will be. The more chronologically irregularly the movement repeats, the more the forming lines will deviate from a straight line or will exhibit gaps.

For each row of the distance matrix, the intersection points of the lines with the row result in the smallest distances, i.e. the greatest correspondence of the intermediate images compared to the intermediate image on which the row is based.

In order to find these intersection points, the lines are in each case approximated or fitted by a curve or spline using an active contour method, also called active contours or snakes. For this purpose, a straight line appropriately shifted parallel to the main diagonal is in each case used as the starting position and a one-dimensional spline, i.e. a one-dimensional polynomial chain, is adjusted to one of the lines, i.e. to its course, by means of a minimization of an associated energy function.

Using the curves or splines determined in this way, the raw data sets on which the intersection points of the lines with a row of the distance matrix are based are determined. From the subgroup of raw data sets determined in this way for a row of the distance matrix, an image is reconstructed which exactly represents a phase of the movement.

Advantageously, the distance matrix is a Euclidean distance matrix. The Euclidean distance matrix is a simple variant of realizing a distance matrix.

Advantageously, the k-space can be scanned using a configuration scheme that ensures a configuration distributed as evenly as possible in the k-space for each associated subgroup of k-space sub-trajectories or spokes.

The scanning can for example be carried out according to an aperiodic configuration scheme.

It is important for the quality of the images that the k-space trajectory, also called the sampling trajectory, is selected such that the angles of a subset of the k-space sub-trajectories on which an image is to be based are distributed as evenly as possible in the k-space. During the measurement of a cyclic movement, there is in particular the risk of beats occurring between the sampling trajectory and the movement so that subgroups of individual k-space sub-trajectories assignable to a movement phase cannot result in a scanning of the k-space and thus in sufficient k-space information.

By an aperiodic scanning, beats of the scanning of the k-space with the cyclic movement can be avoided and the maximum size of the intermediate spaces in the k-space can be minimized in the k-space sub-trajectories on which an image is ultimately to be based. The quality of the tomographic or volume images is thereby improved.

Advantageously, chronologically successive radial or almost radial k-space sub-trajectories (k1, . . . , kx) enclose an angle that corresponds to the golden angle.

The golden angle, i.e. an angle of 137.5° or 222.5°, represents a simple and reliable option for avoiding beats of the scanning of the k-space with the cyclicality of the movement and minimizing the size of the intermediate spaces in the k-space sub-trajectories on which an image is ultimately to be based.

The golden angle ensures angles which are distributed as evenly as possible for each subset of the k-space sub-trajectories which is associated or related based on the movement.

BRIEF DESCRIPTION OF THE DRAWINGS

The method according to the present disclosure is explained with the aid of the drawings. The figures show.

EMBODIMENTS

Figure 1:
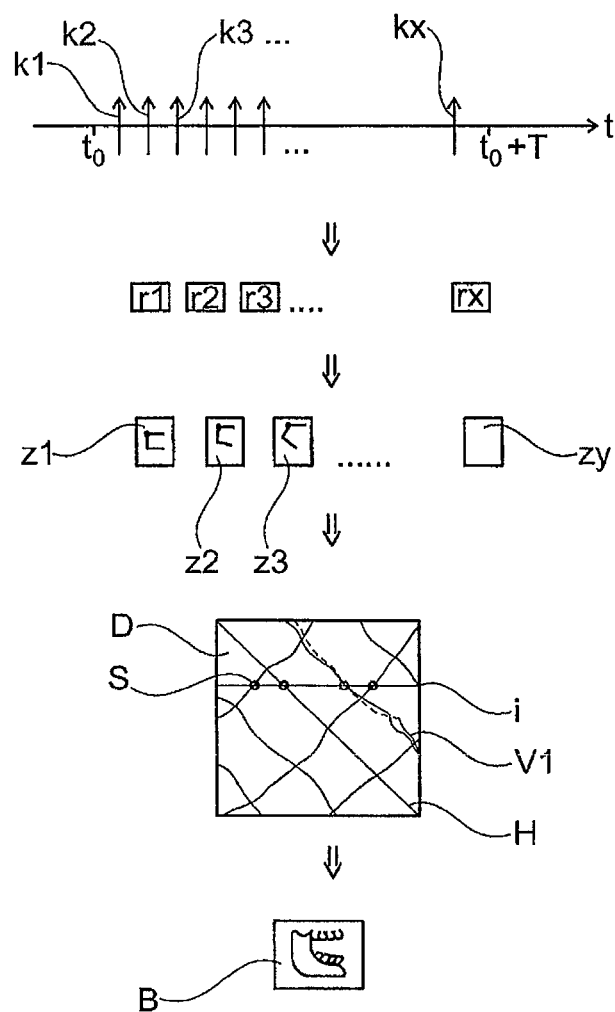
FIG. 1 depicts a schematic representation of the method,
FIG. 2 demonstrates radial k-space sub-trajectories.

FIG. 1 schematically shows the sequence of a method according to the present disclosure at least in parts using the measurement of a masticatory movement. Using an MRT system known from the prior art, a mandibular joint of a patient is measured over a time interval T, wherein the patient performs masticatory movements during the time interval T. During the measurement, radial k-space sub-trajectories k1, k2, k3, . . . , kx are scanned and the measurement data are generated in the form of raw data sets r1, r2, r3, . . . , rx and stored for example one after the other in a storage sector of a storage unit.

Figure 2:
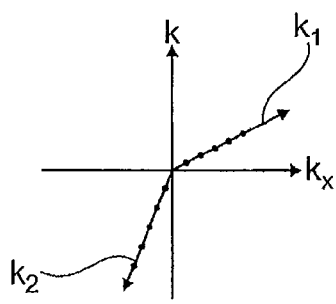

The k-space is for example scanned according to the golden angle, i.e. two chronologically successive radial k-space sub-trajectories k1, k2, k3, kx always enclose an angle that corresponds to the golden angle, i.e. 137.5° or 222.5°, as illustrated in FIG. 2.

The measurement of the masticatory movement of a jaw joint is exemplarily described herein. However, a repeating speech movement or a cyclic opening and closing of the mouth or even other joints in movement, such as a knee joint, can also be measured. However, other moving objects can also be measured, for example, a breathing movement can be measured, where the lung-liver edge can for example be selected as region of interest (ROI).

The configuration of the MRT system used for the measurement depends in particular on the joint or object to be measured or on the radius of movement to be measured of the joint or object. Depending on the point in time when the raw data set r1, r2, r3, . . . , rx was recorded, the raw data set represents a different phase of the movement, such as a closed or completely opened jaw or a slightly opened jaw position during the opening or closing of the jaw.

Since the movement is performed cyclically, i.e. the different phases repeat over the time interval, several raw data sets recorded at different points in time can be used for an image of a certain phase of the movement, the raw data sets respectively representing this particular phase of the movement.

In order to be able to assign the raw data sets r1, r2, r3, . . . , rx to the different movement phases, intermediate images z1, z2, . . . , zy are reconstructed from the raw data sets, said intermediate images at least representing a region representing the movement, also called a region of interest (ROI), with a high temporal resolution. The region or ROI is for example selected around the condyle in the case of the measurement of a jaw joint.

In order to achieve an adequate temporal resolution of the intermediate images z1, z2, . . . , zy, fewer radial k-space sub-trajectories or raw data sets per intermediate image are used than indicated by the resolution and in this way intermediate images with a low spatial resolution or with aliasing artifacts are reconstructed. For example, from a low number of successive raw data sets, subsampled intermediate images can be reconstructed.

In a distance matrix D, such as a Euclidean distance matrix, the distances of the intermediate images z1, z2, . . . , zy to one another, i.e. a distance dimension in each case, are recorded, wherein each row i of the distance matrix D represents the distance, for example, the Euclidean distance, of the intermediate image zi to the other intermediate images z1, z2, . . . , zy as well as to itself. Due to the perfect similarity of each intermediate image z1, z2, . . . , zy to itself, the distance matrix D has a main diagonal H with minimum values. Furthermore, due to the cyclicality of the movement, i.e. each of the different movement phases occurring or being run through several times, the distance matrix D has additional lines of minimum values running parallel and orthogonally to the main diagonal H. These lines run only approximately straight, since the cyclic movement, for example the masticatory movement, is performed continuously but not necessarily uniformly.

Based on the lines of the distance matrix, the intermediate images zj with the highest similarity can be found for each intermediate image zi by determining the intersection points S of the lines with the row i of the distance matrix D. For this purpose, each line is approximated or fitted using an active contour method.

The active contour method approximates a spline, i.e. a polynomial chain, to a contour by minimizing an appropriately defined energy function. The spline is also called curve or function v1, v2, . . . , vz below. A straight line shifted parallel relative to the main diagonal H can be used as the starting value for the active contour method.

Using the curves or functions v1, v2, . . . , vz (shown as a dashed line) determined or fitted for each line of the distance matrix D, the intersections S of the functions with in each case one row of the distance matrix D are determined. In this way, an image B for each row can be reconstructed from the raw data sets r1, r2, r3, . . . , ry on which the matrix elements of the intersection points S are based, each image representing a specific movement phase.

The invention claimed is:
1. A method for producing magnetic resonance tomography images (B) of at least one phase of a cyclic movement, comprising the method steps:
producing raw data sets (r1, . . . , rx) of a cyclic movement during a recording period (T) having k-space sub-trajectories (k1, . . . , kx);
reconstructing a series of at least two intermediate images (z1, . . . , zy) for each region of interest, wherein each of the intermediate images is produced from at least one raw data set (r1, . . . , rx);
calculating a distance matrix D from the series of intermediate images (z1, . . . , zy),
wherein each matrix element D corresponds to the distance of an intermediate image (z1, . . . , zy) of the series to itself or as well as to at least one further intermediate image (z1, . . . , zy) of the series;
producing splines or functions (v1, . . . , vz) for structures of the distance matrix D running parallel and orthogonally to a main diagonal structure H of the distance matrix D by approximating said structures using an active contour method wherein an associated energy function is minimized;
determining an intersection S between the splines or functions (v1, . . . , vz) and entries assigned to an intermediate image zi, of the distance matrix D;

reconstructing at least one image Bi from the raw data sets (r1, . . . , rx), said raw data sets corresponding to said intersection S.

2. The method according to claim 1, wherein the distance matrix (D) is a two-dimensional Euclidean distance matrix.

3. The method according to claim 1, wherein the k-space is scanned using a configuration scheme which ensures a configuration distributed as evenly as possible in the k-space for each associated subgroup of k-space sub-trajectories (k1, . . . , kx).

4. The method according to claim 1, wherein the chronologically successive k-space sub-trajectories (k1, . . . , kx) enclose an angle that corresponds to a golden angle said golden angle being an angle of 137.5° or 222.5°.

5. The method according to claim 1, wherein the structures of the distance matrix D are lines.

6. The method according to claim 1, wherein, in order to achieve a desired temporal resolution of the series of intermediate images (z1, . . . , zy), fewer radial k-space sub-trajectories (k1, . . . , kx) or raw data sets (r1, . . . , rx) per intermediate image are used than is indicated by a predetermined resolution such that intermediate images with a low spatial resolution or with aliasing artifacts are reconstructed.

7. The method according to claim 1, further comprising selecting the region of interest to be a joint in movement or a lung-liver edge.

* * * * *